United States Patent [19]
Bohs et al.

[11] Patent Number: 5,399,256
[45] Date of Patent: Mar. 21, 1995

[54] ELECTROCHEMICAL DETECTOR CELL

[75] Inventors: Curtis E. Bohs, Battle Ground, Ind.; Michael C. Linhares, Groton, Conn.; Peter T. Kissinger, W. Lafayette, Ind.

[73] Assignee: Bioanalytical Systems, Inc., West Lafayette, Ind.

[21] Appl. No.: 178,913

[22] Filed: Jan. 7, 1994

[51] Int. Cl.$^6$ .................... G01N 27/26; G01N 21/00; G01N 31/02

[52] U.S. Cl. ..................... 204/409; 204/412; 204/416; 422/82.01; 422/82.03; 73/61.57; 73/61.58; 73/61.61

[58] Field of Search ............... 204/409, 412, 416, 418, 204/419, 415, 420; 422/82.01, 82.03; 73/61.52, 61.44, 61.56, 61.57, 61.58, 61.59, 61.61

[56] References Cited

U.S. PATENT DOCUMENTS

| | | | |
|---|---|---|---|
| 3,997,420 | 12/1976 | Buzza et al. | 204/415 |
| 4,059,406 | 11/1977 | Fleet | 23/230 |
| 4,092,233 | 5/1978 | Clemens et al. | 204/409 |
| 4,404,065 | 9/1983 | Matson | 204/1 T |
| 4,496,454 | 1/1985 | Berger | 204/402 |
| 4,554,064 | 11/1985 | McClintock et al. | 204/411 |
| 4,628,463 | 12/1986 | Sturrock et al. | 364/497 |
| 4,911,794 | 3/1990 | Parce et al. | 204/409 |
| 5,031,499 | 7/1991 | Kuwana et al. | 73/61.1 OR |

OTHER PUBLICATIONS

Kissinger, Biomedical Applications of Liquid Chromatography–Electrochemistry, *J. Chromatography* 488 (1989), pp. 31–52 no month available.

Shoup, Brunlett, Jacobs & Kissinger: ICEC: A Powerful Tool for Biomedical Problem Solving, *American Lab.*, Oct. 1981.

Hoogvliet, Elferink, Van Der Poel & Van Bennekom, "Design & Characterization of An Electrochemical Ring–Disk Flow" through Detector for Liquid Chromatography; *Analytica Chimica Acta*, 153 (1983) 199–159 no month available.

Fleet and Little, *J. Chromatography*, 12 (1974) pp. 747–752 no month available.

H. Bunasinghm, "Analytical Application of the Wall Jet Detector", *Trends in Anal. Chem.* v. 7 No. 6 (1988) no month available.

Scudder, Pollema & Ruzicka, "The Fountain Cell: A Tool for Flow–Based Spectroscopies," *Anal. Chem.* 1992, v. 64 pp. 2657–2660 no month available.

(List continued on next page.)

*Primary Examiner*—John Niebling
*Assistant Examiner*—Bruce F. Bell
*Attorney, Agent, or Firm*—R. Steven Linne

[57] ABSTRACT

An electrochemical detector cell includes a first block having a planar first working surface, and a first working electrode embedded in the first block member. The first working electrode includes analyte contacting surface disposed co-planarly with the first working surface. A second block member has the second working surface placeable in an opposed, adjacent relation to the first working surface, and has an inlet port disposed an opposed, adjacent relation to the analyte contacting surface of the first working electrode. The second block also includes a coupling means for permitting an analyte delivery tube to be coupled to the second block member to position an end of the analyte delivery tube adjacent to the inlet port. A generally circular circumferential channel for collecting analyte is disposed radially outwardly of the first working electrode. An outlet is disposed at the channel for conducting analyte away from the channel. A reference electrode is disposed in a diametrically opposed relation to the outlet, and a ring-like gasket is placeable between the first and second block members for maintaining the first and second working surfaces in a predetermined spaced relation. The gasket includes a radially inner diameter disposed radially outwardly of the channel. The inlet port, channel, first working electrode, first working surface, second working surface, gasket and outlet port are configured to create a generally centrosymmetric thin layer radial flow path for the analyte across the working electrode, and between the first and second working surfaces, into the channel and out of the outlet port.

27 Claims, 8 Drawing Sheets

OTHER PUBLICATIONS

Shoup, "Liquid Chromatography/Electrochemistry" *High Performance Liquid Chromatography, Advances and Perspectives,* vol. 4, ed. CSABA Horvath, (1986) Academic Press, pp. 121-135 no month available.

Webber & Purdy, "Electrochemical Detection With a Regenerative Flow Cell in Liquid Chromatography", *Analytical Chem.* (1982) v. 54 p. 1757 no month available.

McClintock & Purdy, "Dual Working Electrode Electrochemical Detector for Liquid Chromatography" *Analytica Chimica Acta* 148 (1983) pp. 127-133 no month available.

Bratin & Kissinger, "Glassy-Carbon Amperometric Transducers as Electrochemical Detectors in Liquid Chromatography" *Talanta,* v. 29 pp. 365-370 (1982) no month available.

Kissinger, Bruntlett et al, "Liquid Chromatography with Electrochemical Detection" State of the Art and Future Directions, NBS Special Publication, Trace Organic Analysis: A New Frontier in Anal. Chem. (1978) *Proc. of 9th Materials Res. Sympos.* 10-13 Apr. 1978.

Kissinger, Bratin, et al, "The Potential Utility of Pre- and Post Column Chemical Reactions in the Electrochemical Detection in Liquid Chromatography", *J. Chromat. Sci,* 17 (1979) pp. 137-146 no month available.

Kissinger, "Amperometric & Coulometric Detectors for High Performance Liquid Chromatography" *Anal Chem.* 49 (1977) p. 447A no month available.

Roston, Shoup, Kissinger, "Liquid Chromatography/Electrochemistry Thin Layer Multiple Electrode Detection", *Anal. Chem.,* 54 (1982) pp. 1417A-1434A no month available.

Lunte, Radzik & Kissinger, "An Introduction to the Study of Xenobiotic Metabolism Using Electroanalytical Techniques" *J. Pharmaceutical Sciences,* 79 (1990) p. 557 no month available.

Davis & Kissinger, "Strategies for Determination of Serum or Plasma Norepinephrine by Reverse Phase Liquid Chromatography", *Anal. Chem.* 53 (1981) pp. 156-159 no month available.

Kissinger, Bruntlett & Shoup, "Neurochemical Application of Liquid Chromatography with Electrochemical Detection", *Life Sciences,* 28 (1981) pp. 455-465 no month available.

Bratin, Kissinger et al. "Determination of Nitro, Aromatic, Nitramine and Nitrate Ester Explosive Compounds in Explosive Mixtures and Gunshot Residue by Liquid Chromatography and Reductive Electrochemical Detection", *Analytica Chimica Acta,* 130 (1980) pp. 295-311 no month available.

Shoup & Kissinger, "Determination of Urinary Normetanephrine, Metanephrine, and 3-Metroxytry Amino by Liquid Chromatography, with Amperometric Detection", *Clin. Chem.* 23 (1977) pp. 1268-1274 no month available.

Lunte, Kissinger & Shoup, "Difference Mode Detection with Thin Layer Dual Electrode Liquid Chromatography/Electrochemistry", *Anal Chem,* 57 (1985) pp. 1541-1546 no month available.

Kissinger, "Determination of Biogenic Aminos and Their Metabolites by Liquid Chromatography/Electrochemistry", *Methods in Biogenic Amino Research,* (1983) pp. 75-99 no month available.

Kissinger & Pachla, "Determination of Ascorbic Acid and Dehydroascorbic Acid Using Liquid Chromatography with Ultraviolet and Electrochemical Detection", *Food Technology,* Nov. 1987 pp. 108-111.

ELECTROCHEMICAL DETECTOR CELL

TECHNICAL FIELD OF THE INVENTION

The present invention relates to an electrochemical detector for use in analytical chemistry applications, and more particularly, to a miniaturized electrochemical detector for use in performing analytical determinations on various small sample (e.g. microliter) volumes, to determine both the presence and quantity of analytes contained within the material sample.

BACKGROUND OF THE INVENTION

Many problems in analytical chemistry, and particularly in analytical chemistry for biomedical applications, involve the determination of only a few individual substances (analytes) in very complex samples, such as biological fluids or tissue homogenates. These samples typically contain thousands of individual compounds that are of no interest to the research problem at hand. In addition to the complexity of the samples, the mount of sample volume is often rather limited, particularly in experiments involving laboratory animals. As such, it is often necessary to measure amounts of individual analyte compounds in the picomole range and below. To detect the existence of these compounds of interest, and quantify their presence, an extremely sensitive and selective analytical approach is required.

Recent practice has been to combine existing technologies to achieve the desired end. For example, some analyte samples of interest are particularly susceptible to detection by gas chromatography, mass spectrometry, or some combination thereof. However, many compounds are not readily detectible by either gas chromatography or mass spectrometry. For example, many nonvolatile and thermally labile metabolites of biomedical interest are not directly suitable for gas chromatography/mass spectrometry based analysis. In recent years liquid chromatography/mass spectrometry has overcome several of these problems. However, this technique remains extremely costly and is not suitable for many purposes.

To overcome these shortcomings, researchers often turn to various electrochemical detection systems, and more particularly, to the coupling of liquid chromatography, with electrochemistry. Another technique of interest is to combine in vivo membrane sampling with liquid chromatography/electrochemistry to monitor compounds continuously extracted from living organisms such as laboratory animals.

Combining a liquid chromatography separation system with an electrochemistry detection system to create a combined liquid chromatography/electrochemistry (LCEC) detection system is well known. The basic outline of a conventional LCEC analyzer is shown schematically in FIG. 1.

An LCEC analyzer 10 includes a pump 12 for pumping a mobile phase (such as that contained in flask 14) through a tube 16. Preferably, the pump 12 used for pumping the mobile phase is a constant flow, reciprocating dual piston pump. The pump should provide a flow that is as smooth and pulseless as possible, thereby minimizing baseline noise. An injection valve 20 is provided for injecting the sample into the mobile phase that is flowing through the tube 16. The sample/mobile phase mixture then enters the upstream end 26 of a liquid chromatography column 24, passes through the column 24, and emerges at the downstream end 30 of the column 24. In order to maintain temperature control, the chromatography column 24 is mounted to a heater block 25.

The material that enters the upstream end 26 of the column 24 is very different than that which emerges from the downstream end 30. At the upstream end 26, the sample comprises a sample mixture, wherein all of the various analytes are mixed within the sample. As the sample flows down the column 24, the various analytes contained within the sample migrate at various rates, so that at the downstream end 30 of the column 24, the constituent analytes emerge in generally discrete, separated analyte bands.

Following the separation of components, the eluent (containing both mobile phase and analytes) is conducted through an analyte transfer tube portion 32 to an electrochemical detector cell 34. The electrochemical detector cell 34 typically includes a working electrode, an auxiliary electrode and a reference electrode. A potential is supplied at the working electrode interface by an amperometric controller 36 that also measures the resulting electrolysis current across the sample within the electrochemical cell 34. A recorder 38 is provided for recording the output of the controller 36. Typically, this output consists of a chart graph of electrical current as a function of time. The heated metal block 25 helps to ensure uniformity, and reproduceability of results by controlling the temperature of the mobile phase and the sample flowing through the column 24 and the detector cell 34.

Electrochemical detection is based on a controlled potential and a measured electrolysis current. A predetermined potential difference (usually between (+1.4) and (−1.5) volts, and dependent upon the redox behavior of the analyte to be detected) is applied between the reference and the working electrodes. The applied potential serves as the driving force for the electrochemical reaction that occurs in the detector cell, at the working electrode surface. As the potential of the working electrode relative to the reference electrode becomes more positive, the surface (of the working electrode) becomes a better oxidizing agent (electron sink). Conversely, the more negative the applied potential, the better the working electrode acts as a reducing agent (electron source).

As an oxidizable solute (e.g. norepinephrine) passes over the surface of the working electrode, those molecules immediately adjacent to the electrode surface will be oxidized in a heterogeneous transfer of electrons. The current that results from this exchange of electrons with the surface is monitored as a function of time. Since the rate of material conversion by the electrochemical reaction is proportional to the instantaneous concentration, the current will be directly related to the amount of analyte eluted as a function of time. If the chromatographic condition (mobile phase, flow rate, temperature, etc.) are carefully controlled, amperometric detection can be quite precise, permitting the user to obtain quantitative data at the picomole level (total injected amount) for many compounds.

A wide variety of working electrodes can be used in the electrochemical detector. The electrode used should be physically and chemically inert to the mobile phase at the chosen applied potential. Four electrode surfaces that have been found to be useful are glassy carbon, carbon composites, platinum and mercury. Glassy carbon is versatile because it has excellent resistance to nearly any solvent used in liquid chromatography, and may be used over a wide potential range. Carbon composites have been used as a reliable surface for many years for the determination of catecholamines and related substances. Platinum is especially useful for the determination of hydrogen peroxide. Mercury provides an extended negative range of potential, but has very limited applications when using positive potential.

An early example of an LCEC cell was proposed by Fleet and Little. See, B. Fleet and C. J. Little, *J. Chromatography* 12 (1974) at pp. 747-752. In the Fleet and Little cell, eluent is directed as a "jet" onto a single working electrode. The Fleet and Little cell is an example of a "wall jet" type cell wherein a probe-like jet having a relatively smaller diameter is positioned to direct eluent onto a relatively larger diameter working electrode. To achieve wall jet characteristics, there must be sufficient volume to permit the eluent that is directed onto the electrode to flow radially and axially away from the point of impact on the electrode.

An example of another known prior art electrochemical cell is shown in Shoup, Bruntlett, Jacobs, and Kissinger, "LCEC: A Powerful Tool For Biomedical Problem Solving", *American Laboratory*, October, 1981. This article discloses a thin-layer amperometric transducer for use in liquid chromatography/electrochemistry applications. The device shown in the Shoup article uses a thin layer "cross-flow" pattern, wherein the sample enters the detector cell at one side of a working electrode, flows across the working electrode to the other side of the working electrode, and then flows out through an outlet robe. Once the material flows out the outlet tube, it passes over a reference electrode, and then is lead to a collection tube. Electrochemical detector cells of the type described above have been manufactured and marketed since 1974 by Bioanalytical Systems, Inc. of West Lafayette, Ind., the assignee of the instant invention.

An improved, later generation thin-layer electrochemical detector for use in LCEC applications is shown in Kissinger, "Biomedical Applications of Liquid Chromatography-Electrochemistry", *Journal of Chromatography*, Number 488 (1989) at pages 31-52. The device discussed in this article was invented by Ronald Shoup, a co-worker of the applicants in 1985, and is manufactured by Bioanalytical Systems, Inc. of West Lafayette, Ind., the assignee of the present invention. The Shoup device includes an auxiliary electrode block, and a working electrode block. Between the two blocks is a gasket which, when assembled includes a "cross-flow" path defined between the surfaces of the auxiliary and working electrode blocks, and the interior "cut out" portion of the gasket. Sample exiting a liquid chromatography column flows through an analyte transfer tube and around a mobile phase preheater for maintaining a desired temperature. The sample then passes through an inlet in the auxiliary electrode onto a working surface of a working electrode block. The analyte then flows linearly across the working electrode to the opposite side of the working surface of the working electrode block, and then out the outlet of the block. One of the very useful features of the Shoup device is that it includes a clamp system to facilitate replacement of the electrodes in the device.

A wide variety of working electrode configurations can be used with both flow cells described above, including a single working electrode, a dual parallel electrode, and a dual series electrode. Electrochemical detector cells of the type described above are suitable for a wide range of applications, have proven to be great commercial successes and are widely accepted by the scientific community.

However, room for improvement still exists. This need for improvement is driven largely by the desire to perform analytical operations on smaller and smaller sample volumes. Originally, the electrochemical detector cells described above were used with chromatography columns that were between about 3 and 10 millimeters in diameter, and through which liquid flowed at rates from about 1 to 5 milliliters per minute. Today, liquid chromatography has evolved in which "microbore" chromatography columns are used having an internal diameter of 1 millimeter or less. Some chromatography columns even have internal diameters of several tens of micrometers. Examples of such microbore chromatography columns are the SEPSTIK series of chromatography columns manufactured by Bioanalytical Systems, Inc.

The use of such small volumes of sample material is not always one of choice. In biomedical applications, compelling advantages exist for using much smaller volumes of material. For example, certain biological systems may only be able to yield very small quantities of fluid. Other situations exist wherein it is desirable for the organism to only withdraw such small volumes of fluid.

Because of the small size of the columns, the flow rate through these microbore chromatography columns is dramatically reduced, as compared to the flow rates used for traditional liquid chromatography columns. For example, many of these microbore chromatography columns have internal diameters of about 1 millimeter and typically utilize flow rates therethrough on the order of between about 50 and 200 microliters per minute of material.

As a result of these small flow rates, the volume in which the sample analytes are contained as they elute from the liquid chromatography column is much smaller. Because of this, conventional electrochemical detector devices must be improved to accommodate these smaller volumes without distorting the concentration profiles for the substances eluting from the column. It has been found by the applicants that the "cross-flow" designs used in the two detector cells discussed above can be improved upon for detecting analytes at these small volumes and flow rates.

It is therefore one object of the present invention to provide an electrochemical detector cell that has utility when used to detect the presence and quantity of analytes in very small sample volumes. It is also an object of the present invention that such detection be done in a reliable and repeatable manner by the detector cells.

A related problem experienced with some, prior art detectors is the amount of "dead volume" in the analyte transfer tube portion of the LCEC detector between the downstream end 30 of the liquid chromatography column 24, and the working electrode of the detector cell 34. It is preferable to minimize dead volume space. In this dead volume space, the sharp bands of analyte that emerge from the downstream end 30 of the liquid chromatography column 24 have a tendency to spread out, and become less defined and concentrated as the material moves through the dead volume. The amount of definition loss for the separated bands that occurs is related to the amount of dead volume. Although this distortion of the bands is not critical when using relatively larger volumes of fluid, it becomes much more critical when the volume that contains the analytes and the flow rate are smaller.

It is therefore also one object of the present invention to provide an electrochemical detector cell that minimizes dead volume between a liquid chromatography column and the working electrode.

Another way in which known electrochemical detector cells can be improved is to make the cells compatible with arrangements wherein multiple detector cells are used. Often a sample of interest will contain a variety of analytes whose presence and quantity are desired to be determined. In many situations, not all of the analytes of interest can be determined using only one electrode, or using only one detector cell. For example, some analytes must be detected using an oxidation reaction, whereas others must be detected using a reduction reaction. In such cases, a single electrode, or a single detector may not be capable of detecting both the oxidation-requiring analyte, and the reduction-requiring analyte. To do so requires either a series of electrodes, or a series of detector cells.

One difficulty with some known prior detectors is that they generally were not well suited to being used in series with other detectors. Many were not suitable because they contained a large volume area into which the analyte flowed. For example, wall jet type electrodes usually required a relatively large volume area immediately downstream in the flow path from the working electrode. Others used a liquid junction reference electrode that required a large volume area.

When an analyte flows into such a large volume, the analyte material tends to mix with other analytes in the sample in the large volume, thus disbursing the nice, relatively "tight" band of analyte that emerged from the liquid chromatography column.

It is therefore also an object of the present invention to create an electrochemical detector cell that helps to better preserve band integrity of an analyte during the passage of a band of analyte through the detector cell, and thereby improve the ability of the detector to be used in an arrangement that includes a series of detector cells.

In addition to its use with liquid chromatography columns, the electrochemical detector cell the present invention also has utility in connection with microdialysis and ultrafiltration in "in-vivo" sampling systems. Microdialysis sampling systems typically involve the use of a probe that can be placed into a living organism, such as a brain, blood vessel, duct or other tissue. The microdialysis probe typically includes a tube having a selectively permeable membrane, through which the body fluid of interest can pass. A perfusion fluid is flowed into the probe past the dialysis membrane to help pick up molecules diffusing through the wall of the selectively permeable membrane. The constant flow of the perfusion fluid through the probe creates a concentration gradient across the dialysis membrane. Chemicals in the extracellular fluid of the surrounding tissue will diffuse across this membrane under the influence of this gradient. Chemicals can also flow from the perfusion fluid into the tissue according to the same principle.

A technique related to microdialysis is ultrafiltration. Ultrafiltration is generally similar to microdialysis. However, instead of the use of a concentration gradient, fluid is extracted from the surrounding tissue by the application of a vacuum to the dialysis membrane.

Both microdialysis and ultrafiltration probes can be placed into living tissue to study the metabolism of a conscious, moving animal. Determination of the concentration and variety of small molecules in a microdialysis or ultrafiltration sample is then possible, to permit the user to obtain a "real time" analysis of the concentration of analyte within the living organism. For example, a rat can be fed a material, such as the drug acetaminophen. Brain tissue can then be sampled through microdialysis to determine the time required for the acetaminophen to move from the animal's digestive tract to a particular part of the animal's brain. Through studies such as this, the efficacy of a drug can be studied and determined. Once the material is removed from the microdialysis or ultrafiltration probe, it can be transferred to an electrochemical detector cell, wherein the presence and quantity of the analyte of interest can be detected.

One difficulty with detecting such materials is that the volume of sample and analyte withdrawn from a living organism is typically also very small, usually only a few microliters. It is therefore also one object of the present invention to provide an electrochemical detector cell that is well suited for use with the small volumes of analyte available in connection with microdialysis and ultrafiltration techniques.

SUMMARY OF THE INVENTION

In accordance with the present invention, an electrochemical detector cell is provided for detecting the presence of an analyte in a material sample. The detector cell comprises a first block member having a first working surface, and a first working electrode means disposed on the first working surface. A second block member is provided having a second working surface that is placeable in an opposed, adjacent relation to the working surface of the first block member, and an inlet means having an inlet port disposed in an opposed, adjacent relation to the first working surface. A channel means is provided for collecting analytes. The inlet port, channel means, first working electrode means, first working surface and second working surface are configured to cream a generally centrosymmetric thin layer flow path for the analyte across both the working electrodes, and between the first and second working surfaces.

In a preferred embodiment, the first working electrode means includes an analyte contacting surface disposed generally co-planar with the first working surface. The analyte contacting surface has a diameter of between about 5 and 50 times the diameter of the inlet port. The inlet means includes a coupling means for permitting an analyte delivery means (such as a liquid chromatography column) to be coupled to the second block member to position an end of the analyte delivery means adjacent to the inlet port.

Additionally, the channel means preferably comprises a generally circular channel disposed radially outwardly from the inlet port. The channel means collects analyte after the analyte has passed over the working electrode. The channel means includes an outlet port for conducting analyte from the detector cell.

One feature of the present invention is that the device is configured to permit a centrosymmetric, radial thin layer flow path within the electrochemical detector cell, and across the working electrode. This feature has the advantage of providing a flow path that increases the residence time of the analyte on the working electrode. The centrosymmetric, radial flow of the analyte across the electrode decreases the linear velocity of the analyte as the analyte flows radially outwardly on the working electrode from the center of the electrode. This increase in residence time helps to improve the sensitivity of the device, to make it more capable of detecting smaller quantities of analyte materials.

Another feature of the present invention is that the device is constructed so that the downstream end of an analyte delivery device (such as a liquid chromatography column) can be placed directly adjacent to the inlet port of the device, which itself, is very close to the working electrode. This feature has the advantage of reducing the dead volume between the analyte delivery apparatus and the working electrode. This low dead volume helps to better preserve the integrity and the "tightness" of the "bands" of analyte that are eluted from the liquid chromatography column. The applicants have found that the integrity and discreetness of the bands deteriorates as a function of the distance and volume between the downstream end of the chromatography column, and the working electrode. By reducing this dead volume, the present invention helps to maintain the band shape and enhance the sensitivity of the device, thus lowering the levels of analyte that can be detected by the device.

It is also a feature of the present invention that the centrosymmetric radial flow path within the device is used in conjunction with a circular channel for gathering analyte after it has passed over the working electrode, and directing this analyte to an outlet. The device avoids the use of large volume areas that form "pools" which can dramatically dilute the analyte bands and mix them together. This configuration has the advantage of helping to maintain the integrity of the bands of analyte, even as the analyte is being passed through the outlet. By maintain band integrity all the way through the electrochemical cell, it makes it possible for the user to place another detector (e.g. optical, electrochemical, mass spectrometry etc.) downstream from the electrochemical cell, and to examine the relatively in-met band downstream in the downstream detector. In some cases it is desirable to collect the separated bands in a fraction collector downstream from the detector cell. Some prior art devices known to the applicants tended to induce a mixing of the analytes within the electrochemical cell, thus rendering the material generally unsuitable for further analysis downstream from the electrochemical cell.

Further features of the invention include the use of a reference electrode without a liquid junction, (e.g. Ag-/AgCl), and the use of multiple working electrodes within a single electrochemical cell detector.

These and other features of the present invention will be apparent to those skilled in the art upon a review of the detailed description of the preferred embodiment of the present invention, believed by the applicants to represent the best mode for producing the present invention, described below.

DETAILED DESCRIPTION OF THE INVENTION

Figure 1:
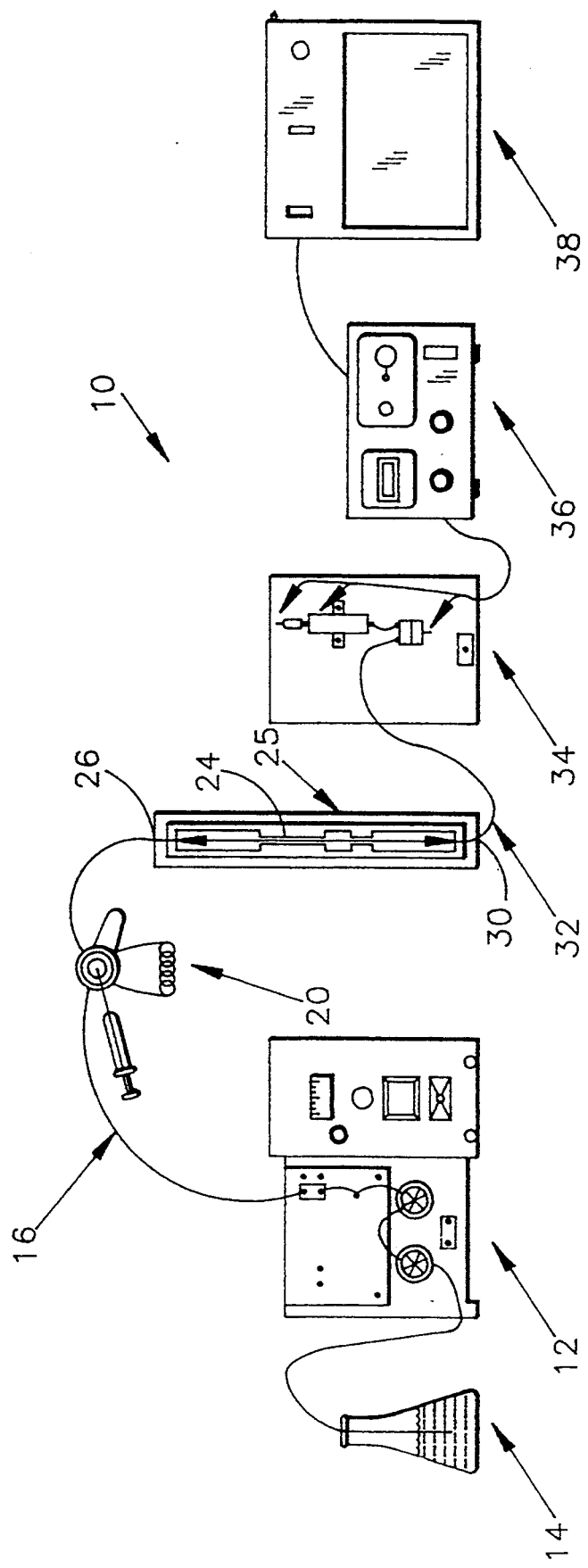
FIG. 1 is a schematic view of a conventional liquid chromatography/electrochemical analyzer set-up.
Figure 2:
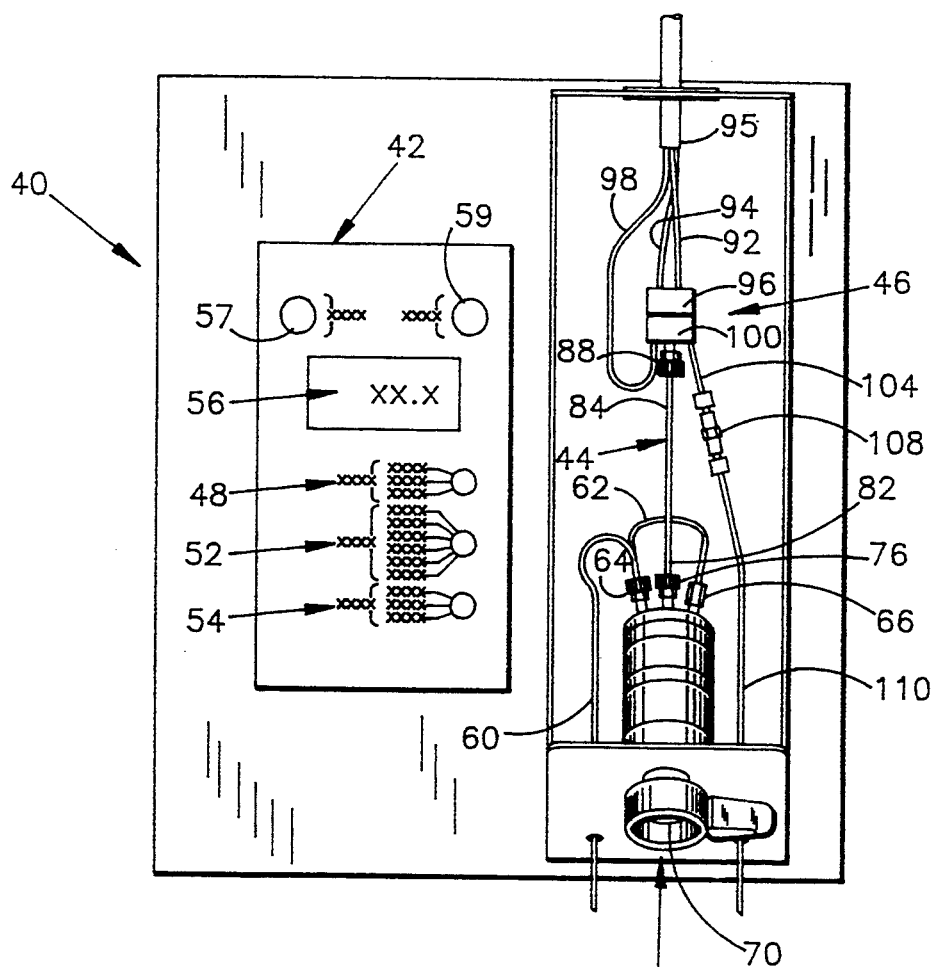
FIG. 2 is an elevational view of an injector, microbore column, and electrochemical defector cell, comprising a miniaturized LCEC system.

A controller unit 40 that includes an electrochemical detector cell 46 is shown in FIG. 2. The controller unit 40 combines, and includes the injector 20, column 24, electrochemical detector cell, and controller 36 of the LCEC apparatus shown in FIG. 1. Controller unit 40 is designed to be used with a pump 12, mobile phase, and a strip chart recorder 38, such as those shown in FIG. 1. Preferably, a computer (not shown) is coupled to the controller 40 to permit the user to better record, process or display the data received from the cell 46. The controller unit 40 includes a control panel 42, a rotary sample injector valve 43, a chromatography column 44, and an electrochemical detector cell 46. The control panel 42 includes a series of knobs to permit the user to adjust the parameters of the device 40. These knobs include a display knob 48 for permitting the user to adjust the function displayed by the liquid crystal display (LCD) 56, a range adjuster knob 52, to permit the user to adjust the various potential ranges applied to the electrodes of the electrochemical detector cell 46, and a cell potential adjustment knob 57 for permitting the user to adjust the applied potential to a value such that particular analyte(s) of interest will be detected.

Preferably, the device also includes an "offset" adjustment knob 59. The purpose of the offset adjustment knob 59 is to counter balance the steady-state background current which exists prior to sample injection and between analyte bands. Examples of controllers that will function with the present invention are the model numbers LC-3C, LC-3D, LC-4C, and BAS 200 controllers manufactured by Bioanalytical Systems, Inc. These controllers are uniquely designed such that they can be used together for multichannel devices. For example, three BAS model LC-3C controllers can provide three channels of data in parallel when a five electrode system is used comprising one reference, one auxiliary and three working electrodes.

An inlet tube 60 is provided for conveying mobile phase from a mobile phase reservoir 14 and pump 12 (FIG. 1). The downstream end of the inlet tube 60 terminates at the valve stator (not shown). Mobile phase is injected into the sample injector 43 into loop 62 via injector port 70. The sample injector 43 is provided for enabling the user to inject the sample into a flowing stream of mobile phase material. The sample injector 43 includes an injector port 70 that is designed for receiving an injection means, such as a syringe that contains the sample of interest. The controller unit 40 also can include a heating means for controlling the temperature of the mobile phase, injected sample, column 44 and detector cell 46.

Although no heater is shown in the drawings, it preferable to use a heater, as it is desirable to control the temperature of the components and the sample and mobile phase materials flowing through the components. It is desirable to control the temperature, in order to ensure optimum results, and to ensure experimental precision from experiment to experiment. An example of an injector port that will function with the present invention is the BAS UNI-JET injector manufactured for Bioanalytical Systems, Inc. by Rheodyne, Inc.

An outlet fitting 76 is provided for coupling the upstream end 82 of the liquid chromatography column 44 to the sample injector 43. The liquid chromatography column 44 shown in FIG. 2 is preferably a SEPSTIK microbore chromatography column manufactured by Bioanalytical Systems, Inc. The SEPSTIK microbore columns comprise liquid chromatography columns especially adapted for separating analytes in microliter sized samples. The typical dimensions of such a microbore column are 50–100 mm in length by 0.3–1 mm in diameter. The packing "stationary phase" materials placed in the microbore columns include things such as C-2, C-8, C-18, and phenyl-modified, silicas, cyano (both silica-CN or $A_2O_3$-CN), or the like. The packing materials typically have particle sizes in the 3 to 8 micron range, and a pore size in the 60 to 300 angstrom range. In addition to the packing materials discussed above, microbore liquid chromatography columns having customized packings can also be prepared.

The downstream portion of the microbore liquid chromatography column 44 is coupled to a column fitting 88. The column fitting 88 couples the downstream portion 84 to the auxiliary (second) block 100 of the electrochemical detector cell 46.

An outlet tube 104 is provided for carrying away reacted analyte from the electrochemical detector cell 46. The outlet tube 104 terminates at a nut-like connector 108. The nut-like connector union 108 connects the downstream end of the outlet tube 104 to a downstream outlet tube 110. The downstream outlet tube 110 can carry the reacted analyte to a disposal vessel. As will be described in more detail below, the present invention also enables the downstream outlet tube 110 to carry the reacted analyte sample to another detection cell, a mass spectrometer, or an optical detector disposed downstream in the sample flow path from the electrochemical detector cell 46. An advantage achieved by the present invention is that it maintains the integrity of the reacted analyte better than many prior, known devices.

Figure 3:
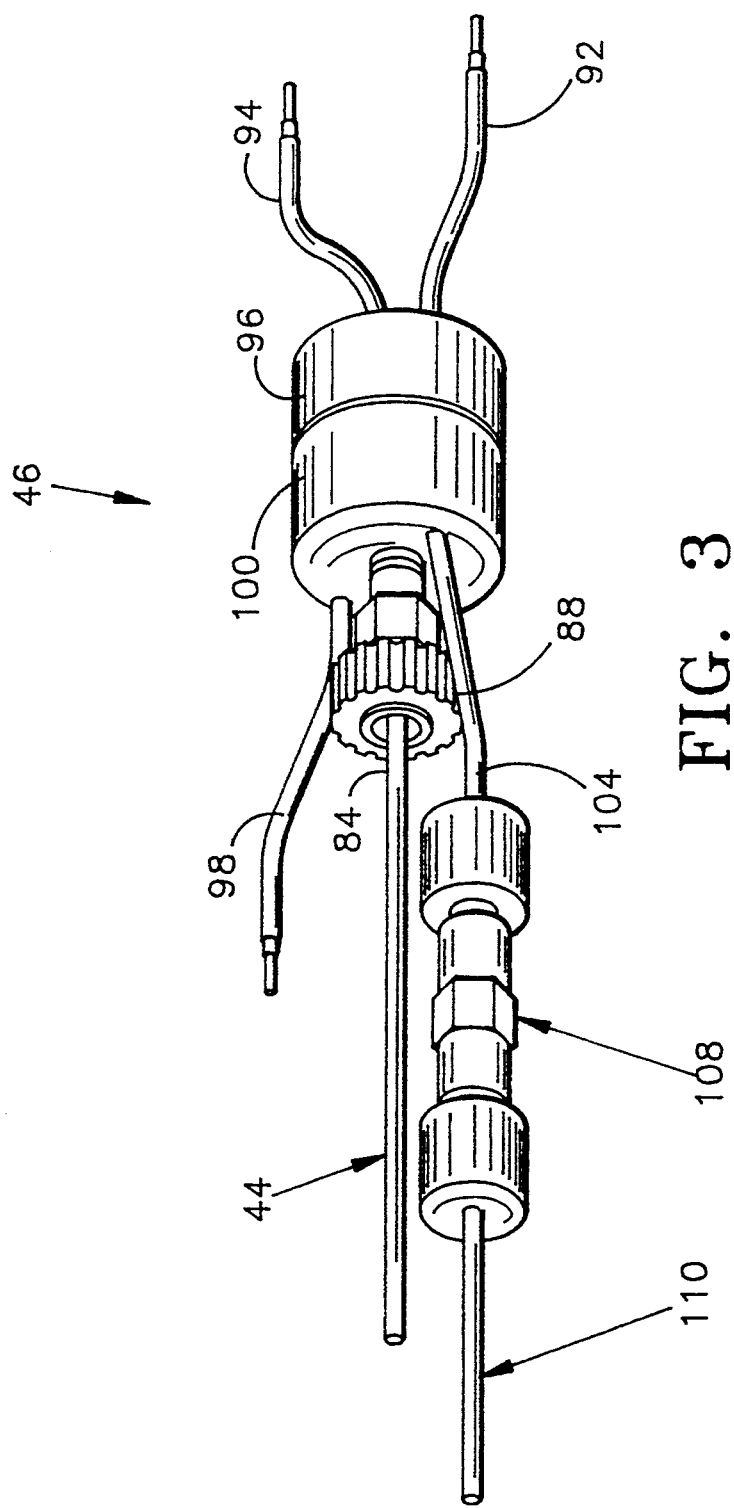
FIG. 3 is an elevational view of an electrochemical detector of the present invention.

Referring now to FIGS. 2 and 3, the electrochemical detector cell 46 includes a first, or working block member 96, and a second or auxiliary block member 100. A working electrode lead 92 leads from the first (working) block 96 to a wire harness 95. A reference electrode lead 94 leads from the first block 96 to the wire harness 95. An auxiliary electrode lead 98 leads from the second (auxiliary) block 100 to the wire harness 95.

The first working block is preferably made from a poly-ether-ether-ketone (PEEK) material. As such, the material is generally non-conductive. On the other hand, the auxiliary block is preferably made from a conductive material, such as stainless steel. Because of its conductivity, the auxiliary electrode lead 98 may be coupled generally anywhere to the auxiliary block 100.

Figure 4:
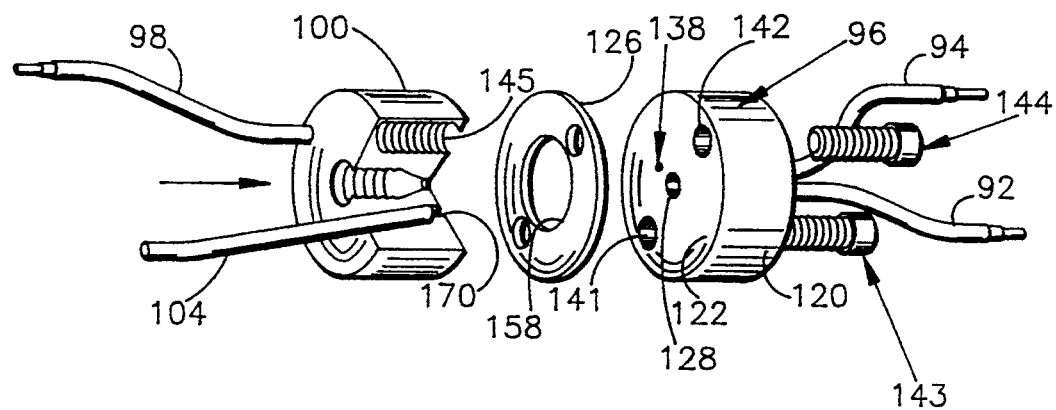
FIG. 4 is an exploded, elevational view of an electrochemical cell of the present invention.
Figure 5:
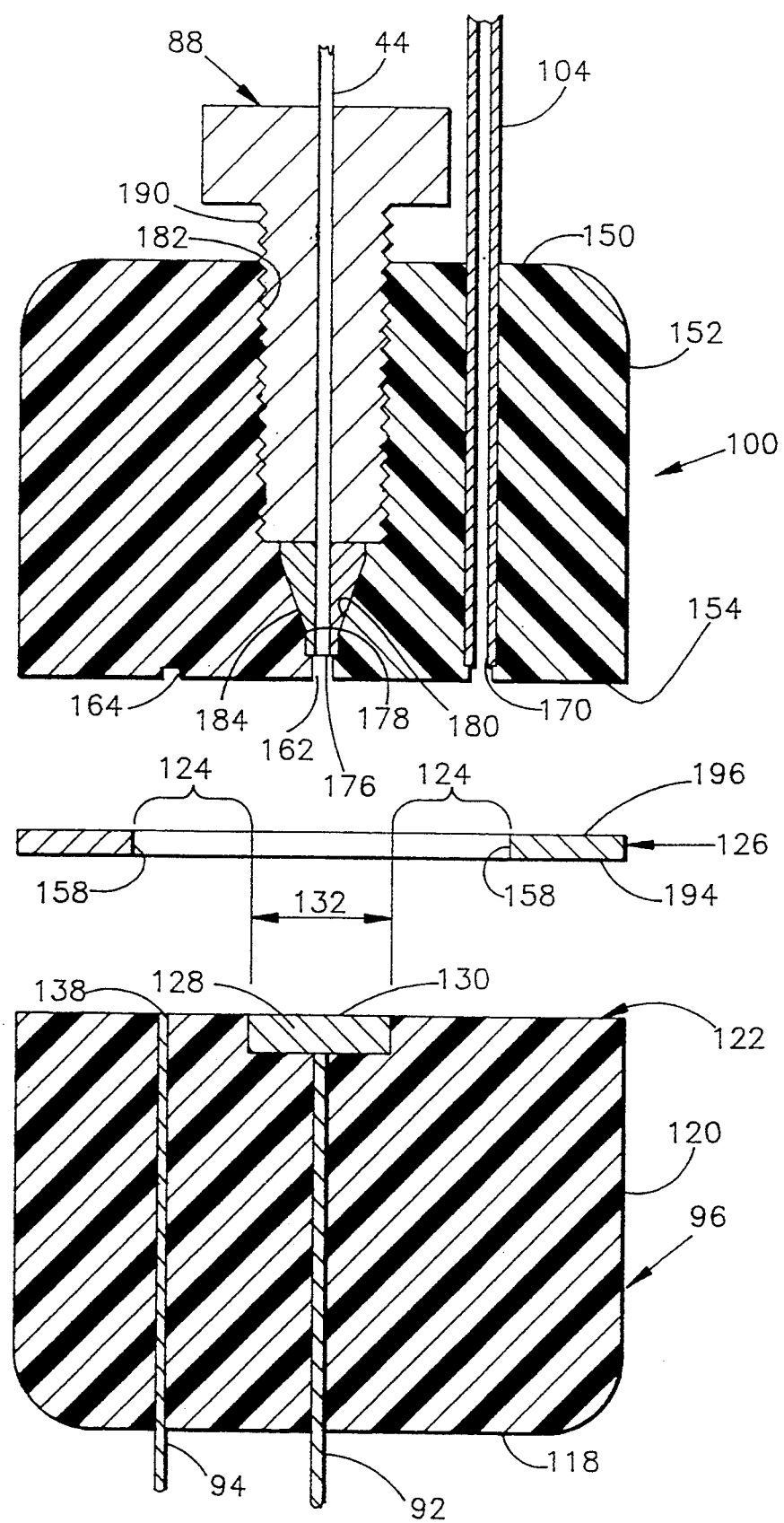
FIG. 5 is an enlarged, exploded, sectional view of an electrochemical cell of the present invention, taken along the longitudinal axis of the electrochemical detector cell.

The working block 96 is best shown in FIGS. 3–5, as generally comprising a solid cylinder having a generally planar base surface 118, a radially outwardly facing cylindrical side surface 120 and a generally planar axially inwardly facing mating surface 122. That working portion 124 of the mating surface 122 disposed generally radially inwardly of the gasket 126 comprises the "working portion" 124 that defines a boundary of the flow path through which the analyte flows in the electrochemical detector cell 46.

The first working block 96 includes a working electrode 128. The working electrode 28 is circular in cross-section, disk shaped in configuration, and generally has a diameter 132 of about between 2 and 6 mm, and a depth of 2–3 mm. The working electrode 128 includes an analyte contacting surface 130 that is generally coplanar with the plane of the first working surface 124 of the first block 96. The working electrode 128 can be made from a wide variety of materials. Materials of choice include glassy carbon, carbon composites, platinum, gold or copper. As best shown in FIG. 4, the working electrode 128 is centered in the middle of the working surface portion 124 of the mating surface 122 of the first working electrode 96. The working electrode 128 is electrically coupled to the working electrode lead 92, so that current can be measured and voltage can be applied to the working electrode 128 by the working electrode lead 92.

A reference electrode 138 is disposed radially outwardly of the working electrode 128, on the working surface 124 of the first working block 96. The reference electrode 138 used in the present invention is preferably a thermodynamic electrode without a porous junction. The electrode consists of silver metal (Ag) coated with a layer of silver chloride (AgCl). In the Nernst equation, the half-cell potential, $E^0$, is a function of the thermodynamic measure at unit activity for all species involved, and the various activities of the component of the half-cell reaction. As will be familiar, the Nernst equation is set forth below:

$$E = E^0 + (RT/nF) \log K,$$

where K is the equilibrium constant for the half-cell reaction written as an oxidation. For the silver/silver chloride electrode, the reaction and corresponding Nernst equation is:

$$Ag + Cl^- \rightarrow AgCl + e^-$$

$$E=E^o+(RT/nF)\log(1/[Cl^-])=E^0-(RT/nF)\log[Cl^-]$$

The activities of the silver wire and silver chloride are unity, and the chloride ion concentration determines the E value. In contrast to known reference electrodes using 3 Molar sodium chloride, the reference electrode of the present invention relies on the chloride ion concentration in the mobile phase. A chloride concentration of 10 mM in the mobile phase results in the potential that is ~100 mV less than, for example, the BAS model RE-4 reference electrode. The small amount of chloride in the mobile phase stabilizes the potential, with only 1 to 2 mV drift per day. However, the silver chloride reference electrode of the present invention can be restored to its original operating potential by recoating the reference electrode with silver chloride. The silver/silver chloride reference electrode 138 is coupled to the reference electrode lead 94 which is itself electronically coupled to the controller unit 40.

One of the more beneficial features of the present invention is that it includes a reference electrode that does not contain a liquid junction. As such, the reference electrode 138 can be made much smaller than many known liquid junction type working electrodes. Additionally, by removing the liquid pool typically associated with liquid junction electrodes, the cell 46 can be better designed to maintain the band integrity of the analyte flowing through the cell 46.

The working block 96 includes a pair of axially extending apertures 141, 142 that are disposed radially outwardly of the working surface 124. The apertures 141, 142 may or may not be threaded, and are provided for receiving connecting bolts 143, 144. The connecting bolts 143, 144 extend through the apertures 141, 142, and are receivable by threaded, axially extending apertures 145 (not shown), that are formed in the second block 100, and which are alignable with the axially extending apertures 141, 142 of the first block member 96. The use of the bolts 143, 144 to hold together the first and second blocks 96, 100 facilitates replacement of the first block 96, and hence it enables the user to more quickly change working electrodes between experiments. This helps to make the user more efficient by reducing his set up time between experiments.

The second block member 100 is preferably made from a conductive material, such as stainless steel. The exterior shape of the second block member 100 is similar to the first block member 96. It is generally a solid cylinder in a shape. The block member 150 includes an axially outwardly facing, generally circular base surface 154, a radially outwardly facing generally cylindrical side surface 152, and an axially inwardly facing mating surface 154. The mating surface 154 includes a working surface portion comprising that portion of the mating surface 154 disposed radially inwardly of the radially inwardly facing surface 158 of the gasket 126. A central inlet port for 162 (FIG. 5) is disposed in the center of the working surface portion of the mating surface 154. The inlet port 162 generally has a diameter of about 1 millimeter or less, and is placed in an opposed, adjacent relation to the center of the analyte contacting surface 130 of the first working electrode 128. A generally circular channel 164 is disposed radially outwardly from the central inlet port 162 on the mating surface 154. The channel 164 is provided for collecting analyte after the analyte has been passed over the working electrode 128, and conducting the analyte to an outlet port 170. The outlet port 170 is disposed within the circular, circumferential channel 164, and is coupled to the outlet tube 104. A portion of the outlet tube 104 extends axially within the second block 100, generally parallel to the longitudinal axis of the block 100.

Figure 7:
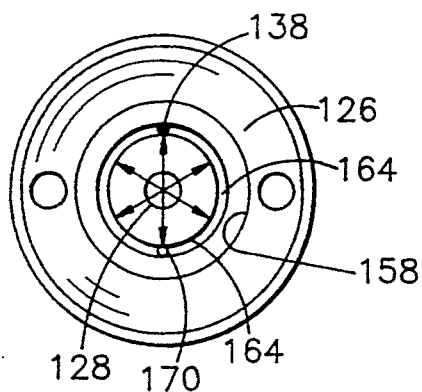
FIG. 7 is a schematic view of the working surfaces of the electrochemical cell of the present invention.

The channel 164 preferably has dimensions of approximately 0.76 mm. deep, by 1.0 mm. wide. The outlet channel 164 is disposed in an opposed, adjacent relation to the reference electrode 138. The reference electrode 138 is placed in a diametrically opposed relation to the outlet port 170, which is also disposed in the channel 164. Turning now to FIG. 7, it will be noted that reference electrode 138 is positioned in the channel 164 at "12:00", whereas the outlet port 170 is disposed at 6:00. This placement is done to minimize the amount of solution that flows over the reference electrode 138 relative to the other areas of the channel 164.

The second block 100 also includes a coupling means for permitting the downstream end of an analyte delivery means, such as the downstream end 176 of the microbore liquid chromatography column 44, to be placed adjacent to the inlet port 162, to minimize the dead volume between (and including) the inlet port 162 and the analyte contacting surface 132 of the working electrode 128. The coupling means includes an inlet means that comprises a fitting receiving cavity formed within the second block member 100. The fitting receiving cavity includes a generally cylindrical, axially inwardly disposed downstream end receiving portion 178 of the inlet means. The downstream end receiving portion 178 is disposed adjacent to the inlet port 162. To help reduce dead volume, the downstream end receiving portion 178 is small. In one preferred embodiment, it 178 has a diameter of about 0.33 mm. and a length of about 1.68 mm. The central fitting receiving cavity extends axially throughout the entire second working block 100. Preferably, the central fitting cavity is positioned centrally in the second block 100 so that its center is collinear with the axially extending axis of the second block 100. The cavity includes a frustoconical portion 180 disposed axially outwardly of the generally cylindrical downstream end receiving portion 178. A generally cylindrical, axially outwardly extending threaded portion 182 is disposed axially outwardly of the frustoconical portion 180.

The frustoconical portion 180 is sized and positioned for receiving a frustoconical shaped ferrule 184 that is placed on the downstream end portion of the liquid chromatography column 44. The ferrule 184 includes an axially extending central passageway for receiving the exterior surface of the liquid chromatography column 44. The coupling fitting 88 has a central axial passageway for receiving the exterior surface of liquid chromatography column 44, and a threaded outer surface 190 for engaging the threaded surface 182 of the inlet passageway of the second block 100.

The ferrule 184 properly positions the liquid chromatography column within a central cavity, so that the downstream end 176 of the liquid chromatography column 44 is disposed at the inlet port 162. The coupling fitting 88 fixedly holds the chromatography column 44 within the central cavity.

A generally ring-shaped gasket 126 is interposed between the mating surfaces 122, 154 of the first and second block members 96, 100. As best shown in FIG. 4, the gasket 126 is generally ring shaped, and includes a radially inner surface 158 that defines the radially outer boundary of the flow path of the sample through the cell 46. Gasket 126 is preferably made from mylar, teflon, or polyethylene. The gasket 126 can be laser cut to ensure that it contains no surface irregularities and to ensure that both the surface 194 of a gasket that contacts the mating surface 122 of the first block 96 and the surface 196 of the gasket that contacts the mating surface 154 of the second block 100, are generally parallel and free from surface irregularities, to reduce the likelihood of leakage between the gasket 126, and the mating surfaces 122, 154 and to maintain generally perfect parallelism between the working surfaces of the first and second blocks 96, 100. This parallelism helps to ensure uniform flow in the flow path.

Preferably, the gasket 126 is cut to be very thin, having a preferred thickness is in the range of about 16 micrometers. By changing the gasket thickness, the user can adjust the linear flow rate of the analyte across the working electrode surface 130 at any given volume flow rate. Generally, the thicker the gasket 126, the slower the linear velocity of analyte flowing across the working electrode surface 130. In this regard, it is important to distinguish between linear velocity and volume flow. Preferably, the volume flow through the cell is constant, and is determined by the pump component of the LCEC apparatus. However, the velocity at which an analyte flows linearly will tend to increase with a thinner gasket, and decrease with a thicker gasket. In this regard, the flow analogy is similar to the flow of a river. Although the volume flow of a river may be constant, the water will have a higher linear velocity in a narrow spot in the river, and will flow more slowly in a wide spot of the river. Thus, the adjustability of the thickness of the gasket enables the user to vary another parameter within his experiment.

Figure 14:
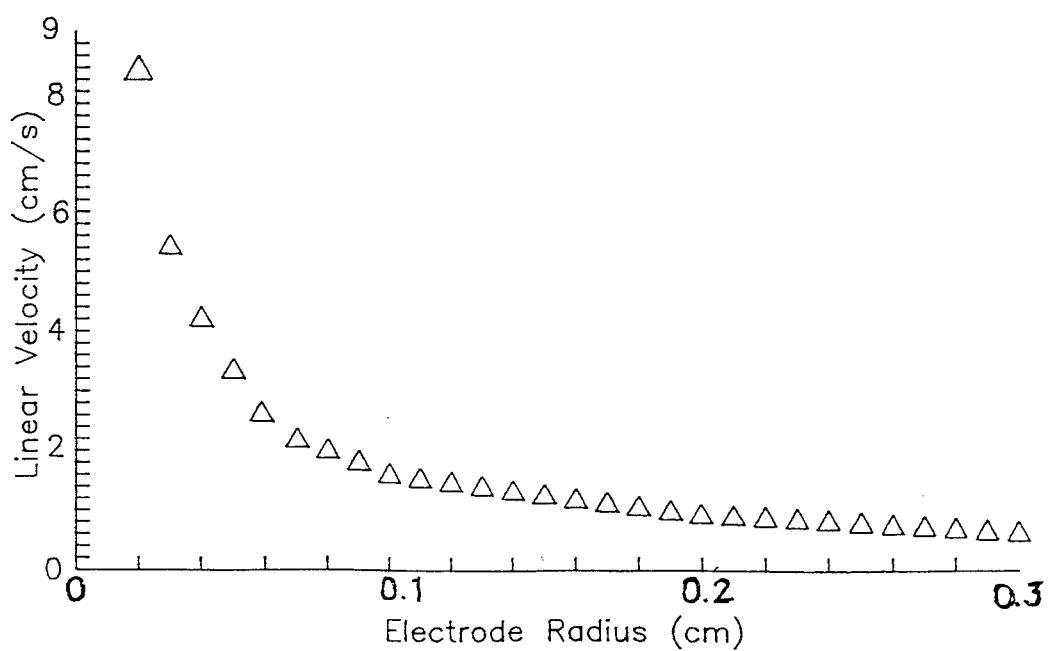
FIG. 14 is a graphical representation of the linear velocity of fluid flowing through the flow path of the electrochemical cell of the present invention which is plotted as a function of electrode radius.

Turning now to FIGS. 5 and 14, when the first and second block members 96, 100 and gasket 126 are assembled into an "electrochemical detector cell sandwich", a centrosymmetric radial flow path is provided for the sample exiting the downstream end 176 of the liquid chromatography column 44. The flow path within the cell is defined by the inlet port 162, the analyte contacting surface 130 of the working electrode, the working surface portions of the first block 96 and second block 100, the radially inwardly facing surface 158 of the gasket 126, the channel 164 and the outlet port 170. Between the working surfaces the first and second blocks 96, 100, the flow is radial and centrosymmetric, as best shown in FIG. 7. That is, analyte flows downwardly out of the inlet port 162, and impinges upon the center of the analyte contacting surface 130 of the working electrode 128. To reduce dead volume, the distance between the downstream end 176 of the analyte of the liquid chromatography column 44 and the analyte contacting surface 130 of the working electrode is generally small, and preferably less than about 2 mm.

Because of the thinness of the gasket 126, the flow of analyte throughout the device does not exhibit "wall jet" characteristics. Rather, the flow exhibits thin layer, radial flow characteristics, wherein the analyte flows radially outwardly across the surface of the working electrode 128, across the working surface portions of the mating surfaces 122, 154, and is collected in the circular, circumferential channel 164. As the reference electrode 138 is positioned in a diametrically opposed relation to the outlet port 170, the flow of analyte over the reference electrode 138 is generally less than at any other point within the channel 164.

The centrosymmetric, thin layer radial flow path of the present invention is fundamentally different from wall jet cell designs and operates according to different mathematical principles. The layer of analyte that travels radially outwardly in the flow path is constricted within a very thin cylindrical volume. This thin layer geometry offers advantages at low flow rates (less than 200 microliters/min) over cross-flow designs or wall jet designs in which the bands would be seriously diluted. The detector cell 46 utilizes the thin layer concept to increase sensitivity (response). It is believed that increased sensitivity is achieved because the reaction of the analyte on the working electrode is more efficient (per unit area of electrode) in the present invention, when compared to a cross-flow design type cell. Examples of experiments illustrating this increased sensitivity can be found in Bohs, Linhares and Kissinger "The UNIJET: A New Electrochemical Detector for Microbore Liquid Chromatography," which is attached to this Application as Appendix B; and Huang, Shoup and Kissinger, "New SEPSTIK Microbore Columns for Liquid Chromatography," which is attached to this application as Appendix C. Both of these articles were written for the Assignee of the present invention, and are to be published after the filing of this patent application in Volume 12, No. 4, January, 1994 issue of *Current Separations*, a journal published by the Assignee.

As the analyte flows radially outwardly across the analyte contacting surface 130 of the working electrode 128, the linear velocity of the analyte is reduced. Thus, the analyte is flowing linearly more quickly at the center of the working electrode 128, than at the outer edges of the surface 130 of the working electrode 128.

FIG. 14 shows the linear velocity relationship as a function of the radius of the electrode at a flow rate of 100 microliters per minute. The linear velocity decreases at increasing distances from the center of the electrode 128, and also decreases with electrodes of larger diameter. This centrosymmetric radial flow of the cell 46 has the advantage of increasing the residence time of the analyte on the electrode surface 130, as compared to cross-flow cells. This increased residence time helps to increase the sensitivity of the electrode 128, and permits detection of volumes, and concentrations possibly not obtainable with known prior, cross-flow electrodes.

Figure 13:
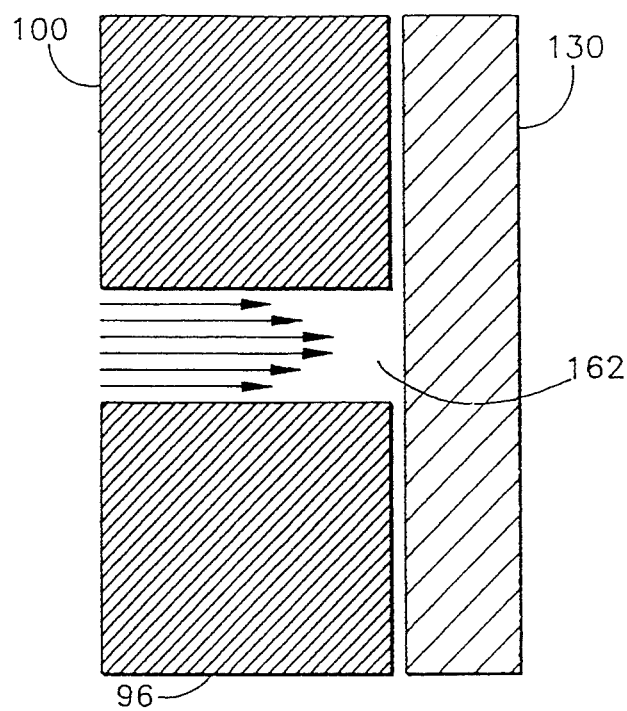
FIG. 13 is a schematic, sectional view of the electrodes of the present invention presented for purposes of showing relative dimensions.

The relative dimensions of the inlet port 162 and electrode surface 130 are important to the operation of the present invention. Turning now to FIG. 13, the relative sizes of the inlet port 162 and working electrode surface 130 are shown. Typically, the inlet port 162 has a diameter of about 1 mm or less, whereas the working electrode preferably has a diameter of at least about 2 to 6 mm. Note also the very small distance between the working surfaces of the first and second blocks 96, 100.

An interesting aspect of the present invention relates to the difference in flow resistance between the potion of the flow both between the working surfaces of the first and second blocks 96, 100, and the flow resistance in the channel 164. As the distance between the opposed working surfaces is typically 16 to 100 micrometers, whereas the channel 164 is typically 1 millimeter in width by 0.76 millimeters in depth, the flow resistance is typically much higher between the working surfaces, than in the channel 164. This flow resistance differential helps to ensure that the flow of analyte through the flow path is both radial and centrosymmetric. It is believed that if the flow resistance in the channel 164 was as great as in the area between the working surfaces, the analyte would exhibit primarily a "cross-flow" characteristic where it would flow primarily from the inlet port 162, across to the outlet port 170.

Another feature of the present invention is that the relatively short distance between the downstream end 176 of the liquid chromatography column 44 and the working electrode analyte contacting surface 130 helps to maintain the integrity of the band of analyte emerging from the downstream end 176. It has been found by applicant that integrity generally disintegrates as a function of volume and distance from the downstream end 176 of the chromatography column 44. By placing the downstream end 176 in such close relation to the analyte contacting surface 130, this degradation is minimized. Additionally, the thin flow characteristics, and relatively small volume contained within the flow path helps to maintain band integrity throughout the flow of analyte through the working cell. The analyte's flow radially outwardly across the working electrode is symmetrical. That is, the large "slug" of a particular analyte will likely maintain a generally constant distance from the center of the electrode as it flows radially outwardly across the analyte contacting surface 130 and working surfaces. For example, all of the "slug" of a particular analyte is likely to maintain its integrity, and enter the channel 164 at about the same time, thus flowing out the outlet port 170, and through the outlet tube 104 in a manner which relatively maintains the integrity of the band compared to earlier devices.

Presented below is Table 1. Table 1 discloses figures for the active volume of material above an electrode, and the linear velocity of analyte through an electrochemical cell, for electrodes having different diameters, and for differing flow volumes.

TABLE 1

| Electrode Diameter (mm) | Active Volume above electrode (nL) (16 um Gasket) | Linear Velocity (cm/sec) 16 um Gasket 10 uL/min | Linear Velocity (cm/sec) 16 um Gasket 100 uL/min | Linear Velocity (cm/sec) 16 um Gasket 1000 uL/min |
|---|---|---|---|---|
| 1 | 12.56 | 0.331 | 3.31 | 33.1 |
| 2 | 50.27 | 0.165 | 1.65 | 16.5 |
| 3 | 113.09 | 0.110 | 1.10 | 11.0 |
| 4 | 201.06 | 0.082 | 0.82 | 8.2 |
| 5 | 314.16 | 0.066 | 0.66 | 6.6 |
| 6 | 452.39 | 0.055 | 0.55 | 5.5 |

First, Table 1 helps to quantify the "thin layer" flow characteristics of the cells setting forth the relatively very small (tens to hundreds of nano-liters) volume quantifies of analyte above analyte contacting surface 130 of a working electrode 128 in a typical cell 46 using a 16 micro-meter thick gasket 126. Table 1 also shows the different linear velocities achieved at the outside edge of various diameter working electrodes 126 that can be used with the cell 46 of the present invention. From Table 1, it can be deduced that as the circumference (radially outer edge) of the analyte contacting surface 130 of the electrode 126 is approached, the linear velocity declines, increasing the effective residence time per increment of electrode area. For example, the time to replace the active volume of analyte above a 3 mm working electrode 126 is 68 milliseconds at 100 microliters per minute. However, at 1 ml/minute, only 6.8 milliseconds are needed. Thus, at lower flow rates, more time is available for the analytes to react at the electrode (assuming the gasket is not varied). The decreased diffusion layer and increased reaction time achievable with the cell 46 of the present invention allows for the conversion of more analyte at the electrode surface. This leads to the conclusion that the electrode reaction is more efficient per unit area at a radial flow electrode compared to a cross flow electrode of the same dimensions when the velocity is uniform across the electrode face.

This centrosymmetric, radial flow permits a wide variety of other working electrode configurations to be used. In particular, multiple electrode configurations can be used. These multiple electrodes may permit the user to perform multi-channel experiments on the sample. For example, a particular analyte can be oxidized on the first working electrode, and reduced on the second working electrode.

Figure 8:
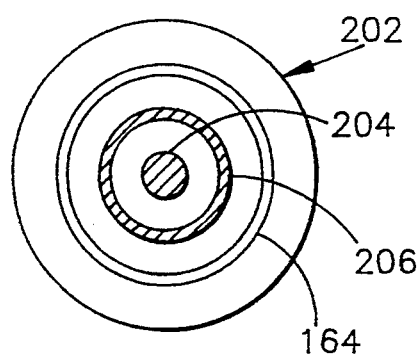
FIG. 8 is a schematic view of the working surfaces of an alternate embodiment of the present invention.

Your attention is now directed to FIGS. 8-12 and 15-17 wherein some alternate embodiment cells (including some multi-electrode cells) are shown. FIG. 8 shows an electrochemical detector cell 202 having a disk-shaped central working electrode 204, that is surrounded by a spaced, second, ring-shaped electrode 206.

Figure 9:
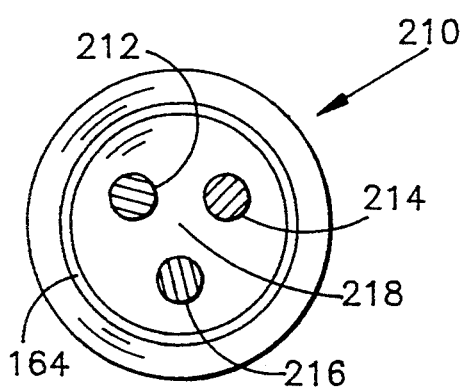
FIG. 9 is a schematic view of the working surfaces of an alternate embodiment of the present invention.

FIG. 9 shows an electrochemical detector cell 2 10 having no working electrode at the center of the working surface 124. Rather, it has a spaced array of working electrodes including a first, second, and third working electrodes 212, 214, 216. Each of the first, second and third working electrodes 212, 214, 216 are separated by about 60 degrees, and are located in a position offset from the center 218 of the electrode.

Figure 10:
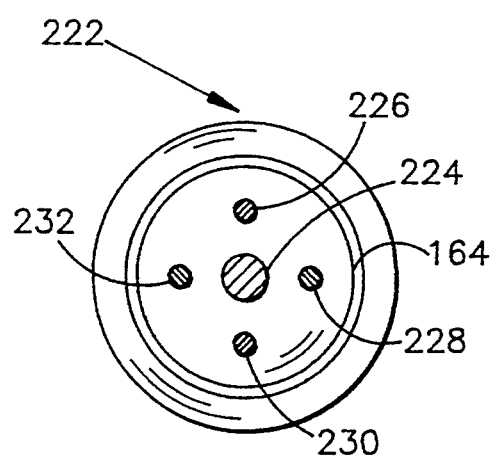
FIG. 10 is a schematic view of the working surfaces of an alternate embodiment of the present invention.

FIG. 10 shows an electrochemical detector cell 222 having a relatively larger central working electrode 224, and four, relatively smaller satellite electrodes, includes a second working electrode 226, a third working electrode 228, a fourth working electrode 230, and a fifth working electrode 232. Each of the four smaller, satellite working electrodes are spaced from the central working electrode 222, and are arrayed at approximately 90 degrees from each other.

Figure 11:
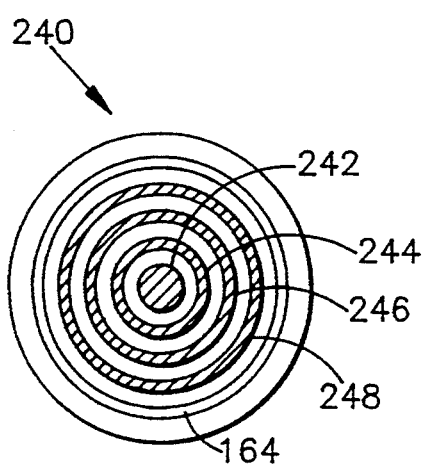
FIG. 11 is a schematic view of the working surfaces of an alternate embodiment of the present invention.

FIG. 11 shows an electrochemical detector cell 240 having a central, disk-shaped first working electrode 242 that is surrounded by three, concentric ring-shaped working electrodes, including second working electrode 244, third working electrode 246, and fourth working electrode 248.

Figure 12:
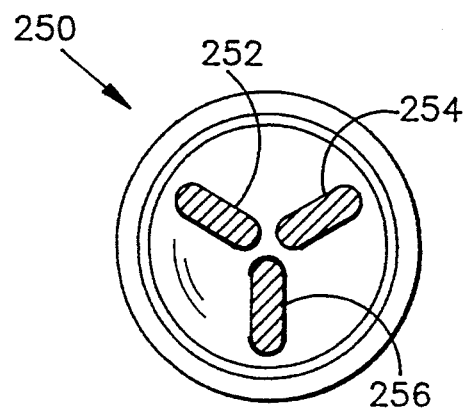
FIG. 12 is a schematic view of the working surfaces of an alternate embodiment of the present invention.

An electrochemical detector cell 250 is shown in FIG. 12 having no central working electrode, but rather having three oval shaped, evenly spaced working electrodes 252, 254, 256. One advantage of using the configuration shown in FIG. 12 is that, as the electrodes are spaced radially outwardly further than a central electrode, the linear velocity of the flow of analyte over the three spatially separated electrodes 252, 254, 256 would generally be less than it would be over a central working electrode, although some analyte will be lost (not detected) between the three electrode segments.

Figure 15:
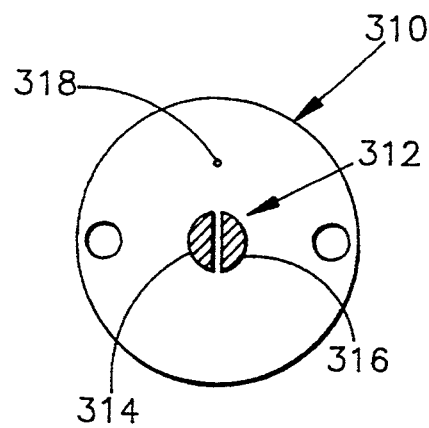
FIG. 15 is a schematic view of the working surfaces of an alternate embodiment electrochemical detector cell of the present invention.

FIG. 15 shows a detector cell 310 having a split-disk working electrode 312 that includes a first working electrode element 3 14, and a second, separate working electrode element 316. A reference electrode 318 is also provided.

Figure 16:
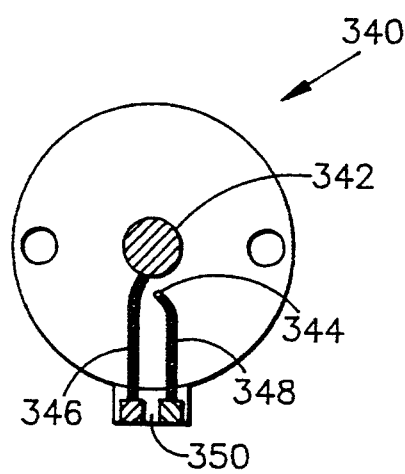
FIG. 16 is a schematic view of the working surfaces of an alternate embodiment of the present invention.

FIG. 16 shows an electrochemical detector cell 340 that has a printed film working electrode 342, and a printed film reference electrode 344. A pair of printed leads 346, 348 convey electricity from the respective working electrode 342 and reference electrode 344 to a connector 350 mounted on the side cylindrical surface of the detector cell 340.

Figure 17:
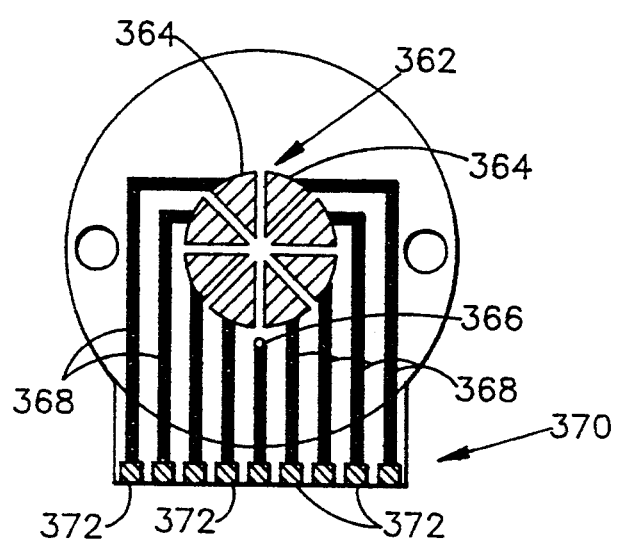
FIG. 17 is a schematic view of the working surfaces of an alternate embodiment of the present invention.

FIG. 17 shows a detector cell 360 that includes a printed working electrode 362 that comprise a series of eight, pie-shaped working electrode segments 364. Detector cell 360 also includes a printed film reference electrode 366. A series of leads 368 are provided for conveying electricity between each of the individual segments 364 of the first working electrode 362, and the reference electrode 366 individually, and a connector 370 having a plurality of "connector pins" 372.

When viewing the multi-electrode (multi-channel) detector cells discussed above, it is important to distinguish between the series multi-channel detector cells, such as those shown in FIGS. 8, and 11, and the parallel multi-channel detector cells, such as those shown in FIGS. 9, 12, 15, and 17. The detector cell 222 of FIG. 10 has both series and parallel aspects. In a series multi-channel electrode cell, at least two of the electrodes are disposed in an upstream/downstream relation. As such, the same "portion" of the analyte is reacted on both upstream and the downstream electrodes. Therefore, the reaction that can and does occur on the downstream electrode is dependant on the manner in which the upstream electrode affects the analyte.

Conversely, in a parallel multi-channel electrode cell, at least two of the electrodes are not disposed in a an upstream/downstream relation. As such, the same "portion" of the analyte is only reacted on one or the other of the two electrodes, but not on both the electrodes. Therefore, the reaction that can and does occur on one of the electrodes is independent of, and generally not affected by the manner in which the other electrode affects the analyte. Turning now to FIG. 10, it will be noted that the central electrode 224 is in series with each of the satellite working electrodes 226; 228, 228, and 232. However, each of the satellite electrodes 226, 228, 230, and 232 are in parallel with each other.

Figure 6:
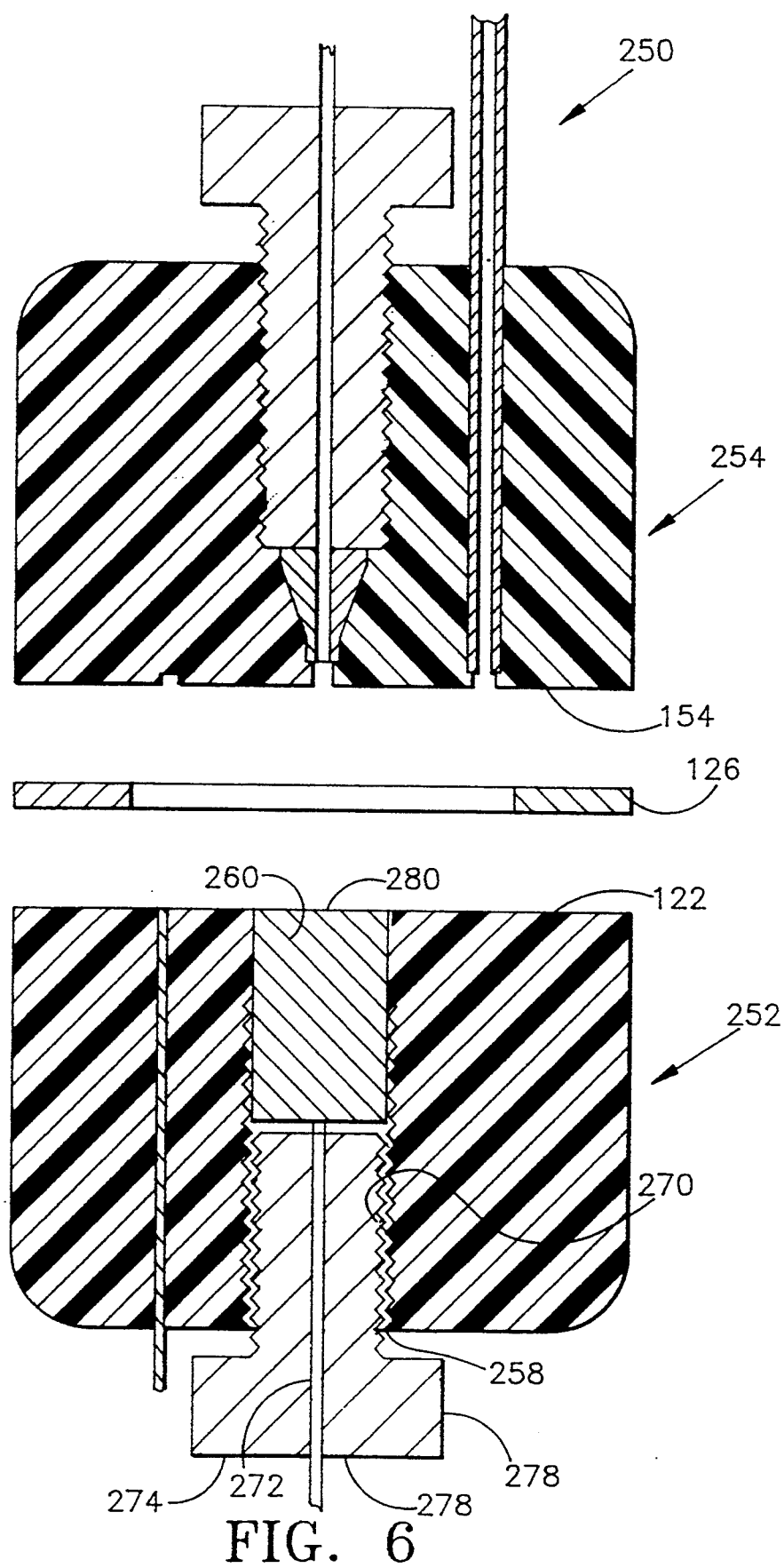
FIG. 6 is an enlarged, exploded, sectional view similar to FIG. 5 showing an alternate embodiment of the present invention.

Turning now to FIG. 6, an electrochemical detector cell 250 is shown having a renewable working electrode 280. Electrochemical detector cell 250 includes a first working block 252, and a second, or auxiliary block 254. Second block 254 is generally identical to second working block 100 as shown in FIG. 5. First working block 252 is generally similar to first working block 96 (of FIG. 5), with the following exceptions. Second working block 254 includes an axially extending central passageway 258 that is provided for receiving a working electrode 260. Working electrode 260 is generally thicker than working electrode 128, to enable working electrode 260 to be renewed regularly. The axially extending passageway 258 includes a threaded surface 270 for threadedly engaging the threaded surface 272 of a fitting 274. Fitting 274 includes a knob 278 for permitting the fitting to be moved axially within the central passageway 258. Preferably, the fitting 274 and working electrode 260 are joined so that axial movement of the threaded fitting 274 causes axial movement of the working electrode 260. Axial movement of the working electrode 260 is induced in order to renew the analyte contacting surface 280 of the working electrode 260, and to adjustably position the analyte contacting surface 280 to ensure that it is a co-planar with the mating surface 122 of the first working block 252.

The working electrode 260 is renewable. As the analyte contacting surface 280 wears out, the fitting 274 can be rotated to move axially inwardly, causing the working electrode 260 to also move axially inwardly. The mating surface 122 of the first working block 252 can then be polished, to create a very planar surface, wherein the analyte contacting surface of the working electrode 260 is both renewed, and is co-planar with the mating surface 122 of the first working block 252.

Discussed below are parameters and factors relating to the operation of the device.

The device should first be assembled. Because of the nature of electrochemical detection, it is important to select a proper environment for the device. Amperometric detection is a highly sensitive technique. Currents measured typically fall in the picoampere or nanoampere range. Hence, smooth operation can easily be influenced by electrical disturbances in the environment. Additionally, since detection is due to a chemical reaction, the response of the cell, and its baseline drift are temperature dependent. The present invention decreases the influence of these problems. However, the following guidelines should be followed when setting up the device. First, all of the components of the LCEC analyzer system should be coupled to the same grounded power line, to eliminate the possibility of a ground loop, which produces base line noise. Additionally, a power line should be selected that does not feed a large number of other amperage consuming devices, such as ovens, centrifuges, and the like. The device should be located on a stable bench, in a room where the temperature remains generally stable throughout the day. The device should also not be placed in very dry areas, or areas that are carpeted, as static electricity can affect instrument performance. Further, areas where radio frequency interference is likely should also be avoided.

The device should be used with a device that delivers a constant flow rate of mobile phase. Ideally, this instrument will be a pump having the precise flow rate characteristics as the Bioanalytical Systems, Inc. model PM-80 pump. The electrochemical detector should be assembled, placing the gasket 126 over the two screws 143, 144 and using the screws to align and join the second block 100 to the working block 96. The pump should be then adjusted to the proper flow rate.

The first chemical component that should be prepared is the mobile phase. Only high-purity solvents and buffer salts should be used in preparing the mobile phase. Water should be type I reagent grade, with a resistivity of greater than 15 megohms. All mobile phases should be filtered through a two micron membrane filter, and should be degassed prior to use. Vacuum filtering may be sufficient to degas the mobile phase. However, an in-line vacuum membrane de-gassing device such in the BAS LC-26 is preferred. This avoids "outgassing" or the production of small bubbles which cause electrical disturbances in the cell current. The liquid chromatography columns 44 should also be washed before use, to remove residual solvents and to give sufficient time for elimination of bubbles from the system. This washing is accomplished by first pumping 100 milliliters of neat acetonitrile through the chromatography column 44, followed by 50 milliliters of a 40:60 acetonitrile/water rinse.

An important parameter of operating the device of the present invention relates to the preparation and servicing of the working electrodes.

In electrochemical detection, the signal being monitored is a direct response to an actual chemical reaction. This is unlike other detectors used with liquid chromatography, such as refractive index, absorbance, and fluorescence which comprise physical measurements. As such, one must consider several variables that can influence the outcome of the chemical reaction, when choosing and servicing a working electrode.

The response of the electrode is dependent on the chemical (electrochemical) reaction variables. These include the electrode surface where the reaction is taking place, the mobile phase (reaction medium) and the compound undergoing the reaction.

The general requirements for electrochemical detection are that the mobile phase be conductive, the working (detector) electrode be chemically inert, and the analyte be electrochemically oxidizable or reducible at the electrode surface in the chosen solution. Solution conductance is met by having an electrochemically inert salt (art ionic conductor) dissolved in the mobile phase. This places some restrictions on the mobile phase composition. Usually, aqueous or partially nonaqueous solutions are used, though totally nonaqueous solutions can be used as long as an appropriate salt is dissolved in them. Since the majority of the liquid chromatographic separations being performed today use reverse-phase packing materials, this requirement is easily met. It is also advisable that the mobile phase be a buffer solution for both electrochemical and chromatographic reasons.

Ideally, the working electrode should be inert to the electrolytic solution, and only respond to the analyte in a thermodynamically defined, potential-dependent fashion. Many times, this is not the case. The kinetics of heterogeneous charge transfer between the electrode and the analyte, in addition to the reactivity of the electrode itself, enter into the situation. Fast electron transfer kinetics characterized by sharply rising voltammograms improves the selectivity of the overall determination.

Electrochemical reactivity can be altered considerably by changing the electrode material. In many cases this can be highly advantageous. The larger hydrogen overpotential characteristic of mercury electrodes in protic solutions extends the attainable negative potential range (past carbon) and makes difficult reduction reactions For this reason, mercury remains the material of choice in these potential regions. However, the reduction of dissolved oxygen, does not occur until well into the negative-potential region on a glassy carbon electrode. Thus, the oxygen over potential of glassy carbon is much better than mercury, and precludes the need for vigorous oxygen purging at moderately negative potentials.

Not all electrode materials will withstand solvents. All carbon-paste formulations are limited to some extent. Glassy (vitreous) carbon, platinum and mercury (amalgamated gold) are resistant to organic solvents. All electrode materials require some surface conditioning or modification before they stabilize to a constant background current level. The conditioning process is observed as a slow decaying current output from the detector after the electrode is turned on. This may take only a few minutes for an electrode that has been switched off momentarily, to as long as a few hours for a freshly prepared glassy carbon electrode at high negative or positive potentials. Longer stabilization times will be required for higher sensitivity operations (i.e. at higher electronic gain or lower current measurements).

The purpose of the reference electrode 138 is to provide a stable, reproducible voltage to which the working (detector) electrode potential may be referenced. A reference electrode may be considered a small battery whose voltage (potential) is determined by the chemistry taking place between a solid conductor (usually a metal salt) and the electrolytic solution around it. Ideally, if a small current is passed through the electrode 138, the potential change is negligible and, in any case, returns to the initial value when the current ceases. In addition, the potential value should not vary with time, and should be reproducible from electrode to electrode.

The present invention in one embodiment utilizes a silver/silver chloride reference electrode 138 without a salt bridge or a liquid junction. The electrode consists of the silver wire coated with silver chloride. The silver chloride coating will be removed each time the electrode is polished. The shiny silver finish will be noticeable. After polishing and rinsing with water, a drop of reference electrode coating solution should be placed on the electrode surface. The solution should be allowed to remain on the electrode 138 for 5 minutes, and then the electrode should be rinsed with water. If the solution performs properly, a silver/silver chloride electrode should be a dull copper color, and uniform in appearance. It is recommended that ten millimolar sodium chloride be used in any mobile phase to increase the stability of the reference electrode, and prevent alterations in its potential. Other reference electrode materials include other silver halides, other silver salts (e.g. silver phosphate) and palladium.

The device of the present invention is useful both in a oxidative mode, and in a reductive mode.

The oxidation of a compound involves the electron transfer from a molecule to the electron surface. The two major advantages of most oxidative applications are that (1) oxygen is not electrochemically active, and (2) solid electrodes can be used. Of course, both of these are definite advantages in the LCEC experiment as well. The working electrode materials most commonly used in oxidative reactions are based on a carbon matrix, typically an anisotropic solid, such as glassy carbon or sometimes an isotropic pyrolytic graphite. Other materials exist and can be used for the LCEC determination, including gold, nickel, silver, platinum, copper and a thin mercury amalgam. A large number of compounds are known to be electrochemically active, and responsive to oxidation type reactions. These compounds include compounds such as phenols, hydroquinones, vanillyl compounds, aromatic amines, indoles, ascorbic acid, xanthines, thiols, macrocyclic antibiotics and phenothiazines.

A large number of functional groups are better analyzed by reductive LCEC than oxidative LCEC. Within a given functional group however, a broad range of reduction potentials exist due to the effects of substituent groups. Generally, the more delocalized the electrons become, the more easily reducible the substance. In addition, electron withdrawing groups on an aromatic ring will enhance the reduction reaction. Examples of functional groups suitable for reductive electrochemical detection include quinones, aromatic nitros, aliphatic nitros, organometallics, n-oxides, azomethines, azo compounds, peroxides, nitrosamines, and thioamides.

Reductive mode LCEC requires some mechanical modifications to remove dissolved oxygen from both the mobile phase and the sample. It is equally necessary to ensure that oxygen does not re-enter the system. Oxygen is removed from the mobile phase in the sample by bubbling an inert gas (e.g., helium or argon) through the solutions. Refluxing the mobile phase at the same time will thoroughly deoxygenate the system. A mechanical arrangement can be set up for this purpose. To deoxygenate the system, plastic tubing should be replaced by stainless steel, because most plastic tubing is permeable to oxygen.

Samples are deoxygenated with helium using a sparging capillary controlled by a needle valve. An optional helium saturation chamber can be filled with water to humidify the gas thoroughly before it enters the sample container.

An example of a working setup used in connection with the present invention is described below. Chromatography was performed using a BIOANALYTICAL SYSTEMS Model No. PM-80 pump either directly for 1 mL/min., or split with a 3.2 ×100 mm. column in order to achieve a 100 microliter/min. flow rate. The PM-80 can be used to accurately pump 100 microliters per minute, without a split if necessary. A BIOANALYTICAL SYSTEMS model LC-4C amperometric controller with a model CC-5 cabinet was used. A RHEODYNE Model No. 9125 injection valve with a loop volume of 5 microliters was used with a standard 3.2 mm. column at 1 mL/min. A RHEODYNE model 7520 injection valve with a 0.5 microliter internal loop was used with the FS SEPSTIK columns and SEPSTIK microbore liquid chromatography columns. SEPSTIK, 100×1 mm. and 150×0.320 mm. columns were packed with C-18-3 micro-meter silica material.

For the separation of catecholamines, the standard mobile phase consisted of 0.1 molar monochloroacetic acid (pH 3.1), 0.5 milli-molar E.D.T.A, 0.65 milli-molar sodium octylsulfate and 3% acetonitrile. The mobile phase was thoroughly degassed and filtered with a 0.2 micrometer Nylon filter before use. Ten milli-molar sodium chloride was added to the mobile phase. All samples were diluted in mobile phase from 0.5 mg/mL stock solutions prepared in 0.1 molar perchloric acid.

Additional information about the operation of the device can be found in a "current draft" *Instruction Manual* that is intended to accompany the device when sold. A copy of the *Instruction Manual* is submitted with this application as Appendix A.

Although the device has been described in detail with reference to certain preferred embodiments, it will be appreciated that variations and modifications exist within the spirit and scope of the appended claims.

What is claimed is:

1. An electrochemical detector cell for detecting the presence of an analyte in a material sample, the detector cell comprising:
   (1) a first block member having a first working surface;
   (2) a first working electrode means disposed on the first working surface;
   (3) a second block member having
      (a) a second working surface placeable in an opposed adjacent relation to the working surface of the first block member; and
      (b) an inlet means having an inlet port disposed in an opposed adjacent relation to the first working surface; and
   (4) a circumferential channel means for collecting analytes that have passed over the first working electrode,
   the inlet port, channel means, first working electrode means, the first working surface and second working surfaces are configured to create a generally centrosymmetric radial thin layer flow path for the analyte across the working electrodes, between the first and second working surfaces and to the channel means.

2. The cell of claim 1 wherein the first working electrode means is disposed in an opposed adjacent relation to the inlet port.

3. The cell of claim 2 wherein the first working electrode means includes an analyte contacting surface disposed generally co-planar with the first working surface, the analyte contacting surface is disposed between about 5 and 100 micrometers from the inlet port means.

4. The cell of claim 2 wherein the first working electrode includes an analyte contacting surface having a diameter between about two and ten times larger than the diameter of the inlet port means.

5. The cell of claim 2 further comprising a second working electrode disposed radially outwardly from the first working electrode means.

6. The cell of claim 5 wherein the second working electrode comprises a ring shaped working electrode.

7. The cell of claim 5 wherein the second working electrode comprises an array of working electrodes disposed at spaced intervals.

8. The cell of claim 1 wherein the first working electrode means includes at least two working electrodes disposed in parallel, and spaced radially outwardly from the inlet means of the second block member.

9. The cell of claim 1 wherein the inlet means includes a coupling means for permitting an analyte delivery means to be coupled to the second block member to position an end of the analyte delivery means adjacent to the inlet port.

10. The cell of claim 1 further comprising a microbore chromatography column having a downstream end, wherein the inlet means includes coupling means for coupling the downstream end of the chromatography column adjacent to the inlet port.

11. The cell of claim 10 wherein the coupling means comprises a fitting receiving cavity formed within the second block member, the fitting receiving cavity including a generally cylindrical axially inwardly disposed downstream end receiving portion for receiving the downstream end of the chromatography column, a frustoconical portion and an axially outwardly disposed generally cylindrical, threaded portion.

12. The cell of claim 11 wherein the inlet port has a diameter of less than about 1 mm, and the distance between the downstream end of the chromatography column and the working electrode is less than about 1 mm.

13. The cell of claim 1 wherein the second block member has a generally planar working surface, and an outlet port disposed adjacent the channel means.

14. The cell of claim 13 wherein the outlet port includes an axially extending outlet passageway, the outlet passageway including means for receiving an outlet tube.

15. The cell of claim 1 wherein the channel means comprises a generally circular channel disposed radially outwardly from the inlet port, and the second block member includes an outlet port disposed at the channel means.

16. The cell of claim 15 wherein the channel is formed in the second block member and is disposed radially outwardly of the working surface, and the outlet port is disposed in the channel.

17. The cell of claim 16 wherein the first block member includes a reference electrode disposed at the channel, and positioned in a diametrically opposed relation to the outlet port.

18. The cell of claim 17 further comprising a generally ring-shaped gasket means having a radially inner diameter slightly greater than the diameter of the channel, the gasket means is placed between the first and second block members to define a radially outer boundary of the flow path.

19. The cell of claim 1 further comprising a ring-shaped gasket member placed between the first and second block members for maintaining the first and second working surfaces in a set spaced relation, the gasket means including a radially inner diameter defining a radially outer boundary of the flow path.

20. The cell of claim 1 wherein the channel means comprises a generally circular channel disposed radially outwardly from the inlet port, and the second block member includes an outlet port disposed at the channel means, further comprising A ring-shaped gasket means having a radially inner diameter slightly greater than the channel, the gasket means is placed between the first and second block members to maintain the first and second block members in a set spaced relation, and to define a radially outer boundary of the flow path, the inlet port, first and second working surfaces, channel means, gasket means and outlet port is configured to maintain the integrity of a band of analyte as it flows from the inlet port, through the flow path and out of the outlet means.

21. The cell of claim 1 wherein the first block member includes a reference electrode without a liquid junction.

22. The cell of claim 1 wherein the first block member includes an axially extending central passageway for receiving the first working electrode means, and electrode positioning means for axially adjustably positioning the first working electrode means.

23. An electrochemical detector cell comprising (1) a first block member having a generally planar first working surface;

(2) a first working electrode imbedded in the first block member, the first working electrode including an analyte contacting surface disposed generally co-planarly with the first working surface;

(3) a second block member having (a) a second working surface placeable in an opposed adjacent relation to the first working surface, (b) an inlet means having an inlet port disposed in an opposed adjacent relation to the analyte surface of the first working electrode, and (c) a coupling means for permitting an analyte delivery means to be coupled to the second block member to position an end of the analyte delivery means adjacent to the inlet port;

(4) a generally circular channel means for collecting analyte disposed radially outwardly of the first working electrode;

(5) an outlet means disposed at the channel means for conducting analyte away from the channel means;

(6) a reference electrode disposed in a diametrically opposed relation to the outlet means; and (7) a ring-shaped gasket means is placed between the first and second block members for maintaining the first and second working surfaces in a set spaced relation, the gasket means including a radially inner diameter disposed radially outwardly of the channel means, wherein the inlet port, channel means, first working electrode, first working surface, second working surface and gasket members and outlet port are configured to create a generally centrosymmetric thin layer radial flow path for the analyte across the working electrode and between the first and second working surfaces, into the channel means, and out the outlet port.

24. The cell of claim 23 wherein the analyte delivery means comprises a microbore chromatography column which separates a sample containing a mixture of analytes into a series of generally discreet analyte bands, the microbore chromatography column including a fitting means which mates with the coupling means for positioning a downstream end of the microbore chromatography column adjacent to the inlet port, wherein the microbore chromatography column, inlet port, first and second working surfaces, gasket means, channel means and outlet port are configured to maintain the integrity of a band of analyte as it flows from the inlet port through the flow path, through the outlet port, and away from the electrochemical detector cell.

25. A working block member electrode for use in an electrochemical detector cell for detecting the presence of an analyte in a material sample, in conjunction with an auxiliary block member having a generally central inlet port, an auxiliary block working surface, and an outlet port disposed radially outwardly from the inlet port, the working block electrode comprising, a first block member having a generally planar first working surface, a first working electrode imbedded in the first block member, the first working electrode including an analyte contacting surface disposed generally co-planarly with the first working surface, and in an opposed adjacent relation to the inlet port of the auxiliary block member, and a reference electrode disposed in a diametrically opposed relation to the outlet means.

26. The electrode of claim 25 further comprising a ring-shaped gasket means placed between the working and the auxiliary block members for maintaining the first working surface and the auxiliary block working surface in a set spaced relation, the gasket means including a radially inner diameter disposed radially outwardly of the outlet path, the first working surface, first working electrode and gasket means, when joined to the auxiliary block member, defining a generally centrosymmetric radial flow path for analyte from the inlet port, across the first working electrode, and between the first working surface and the auxiliary block working surface.

27. An electrochemical detection system for detecting the presence of an analyte in a material sample, the detection system comprising:

(1) a pump means for pumping a material sample through the detection system,
(2) an injector means for injecting the material sample into the detection system,
(3) a temperature control means for controlling the temperature of the material sample,
(4) an electrochemical detector cell comprising
  (a) a first block member having a first working surface;
  (b) a first working electrode means disposed on the first working surface;
  (c) a second block member having a second working surface placed in an opposed adjacent relation to the working surface of the first block member and an inlet means having an inlet port disposed in an opposed adjacent relation to the first working surface; and
  (d) a circumferential channel means for collecting analytes,
wherein the inlet port, channel means, first working electrode means, first working surface and second working surfaces are configured to create a generally centrosymmetric thin layer radial flow path for the analyte across the working electrodes and between the first and second working surfaces; and
(5) a controller means for applying a potential to the working electrode, and measuring and recording the current across the electrodes of the electrochemical detector cell.

* * * * *